United States Patent [19]

Brown

[11] Patent Number: 5,008,448
[45] Date of Patent: Apr. 16, 1991

[54] PREPARATION OF 2-(CHLORO, BROMO OR NITRO)-4-(ALKYL-SULFONYLK)BENZOIC ACIDS AND INTERMEDIATES

[75] Inventor: Richard W. Brown, Richmond, Calif.

[73] Assignee: ICI Americas Inc., Wilmington, Del.

[21] Appl. No.: 470,009

[22] Filed: Jan. 25, 1990

Related U.S. Application Data

[62] Division of Ser. No. 280,787, Dec. 7, 1988, abandoned.

[51] Int. Cl.$^5$ .......................................... C07C 147/107
[52] U.S. Cl. ..................... 562/429; 562/430; 562/125
[58] Field of Search ................... 562/429, 430, 125

[56] References Cited

U.S. PATENT DOCUMENTS

| | | |
|---|---|---|
| 3,639,470 | 2/1972 | Suzuki et al. |
| 3,898,266 | 9/1975 | Feit et al. |
| 4,211,723 | 7/1980 | Koike et al. ........................ 562/833 |
| 4,695,673 | 9/1987 | Heather et al. ...................... 568/310 |

OTHER PUBLICATIONS

Beak et al., J. Org. Chem., 1982, 47; 34–46.

Primary Examiner—Nicky Chan
Attorney, Agent, or Firm—Edwin H. Baker

[57] ABSTRACT

A process for the preparation of 2-(chloro, bromo or nitro)-4-(alkylsulfonyl)benzoic acid and to intermediates used in the process.

5 Claims, No Drawings

PREPARATION OF 2-(CHLORO, BROMO OR NITRO)-4-(ALKYL-SULFONYLK)BENZOIC ACIDS AND INTERMEDIATES

This is a divisional of application Ser. No. 280,787, filed Dec. 7, 1988, abandoned.

BACKGROUND OF THE INVENTION

This invention relates to a process for the preparation of 2-(chloro, bromo or nitro)-4-(alkylsulfonyl)benzoic acids and to intermediates useful in the process.

These 2-(chloro, bromo or nitro)-4-(alkylsulfonyl)-benzoic acids are intermediates useful for the preparation of certain 2-(2-chloro, bromo or nitro)-4-(alkylsulfonyl)benzoyl-1,3-cyclohexanedione herbicides. The 2-(chloro, bromo or nitro)-4-(alkylsulfonyl)benzoic acid is converted to its acid chloride or cyanide and it is reacted with certain 1,3-cyclohexanediones according to the process of U.S. Pat. No. 4,695,673 or U.S. Pat. No. 4,708,127.

SUMMARY OF THE INVENTION

One embodiment of this invention is directed to a process for the preparation of 2-(chloro, bromo or nitro)-4- (alkylsulforyl)benzoic acids, represented by the following reaction steps:

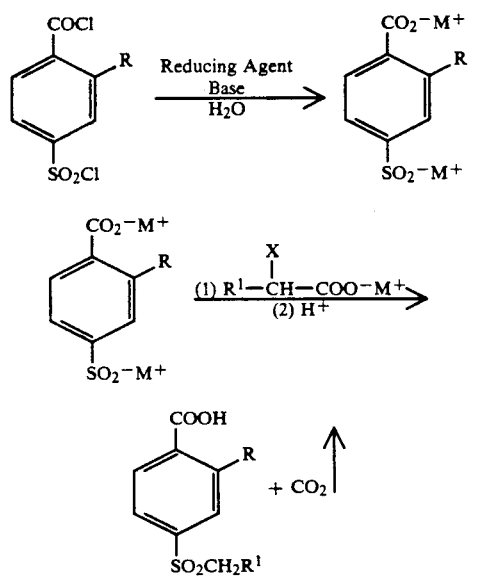

The 2-(chloro, bromo or nitro)-4-(chlorosulfonyl)benzoyl chloride [reactant of Step (1)] can be prepared by the following reaction:

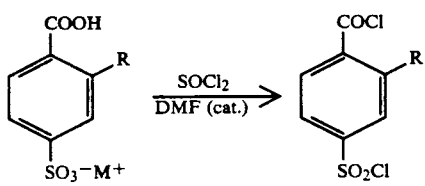

In the above Reaction Steps (1), (2) and (3), R is chloro, bromo or nitro; $R^1$ is hydrogen or $C_1-C_3$ alkyl, preferably ethyl or ethyl, most preferably $R^1$ is hydrogen: M is hydrogen, sodium, potassium or ammonium, preferably sodium; and X is chloro, bromo or iodo, preferably chloro.

A second embodiment of this invention is the intermediate reaction product of Reaction Step (3). This 2-(chloro, bromo or nitro)-4-(chlorosulfonyl)benzoyl chloride intermediate has the structural formula

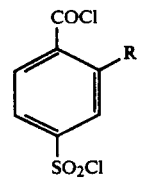

wherein R is chloro, bromo or nitro.

A third embodiment of this invention is the intermediate reaction product of Reaction Step (1). This second intermediate has the structural formula

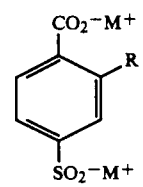

wherein R is chloro, bromo or nitro and M is hydrogen, sodium, potassium or ammonium.

DETAILED DESCRIPTION OF THE INVENTION

Referring to the three reaction steps under the "Summary of the Invention" section, the following is additionally taught.

The process of this invention is depicted by Reaction Steps (1) and (2). Step (3) is provided to a process for the preparation of the intermediate 2-(chloro, bromo or nitro)-4-(chlorosulfonyl)benzoyl chloride which is an embodiment of this invention. Also the intermediate reaction product of Reaction Step (1) is an embodiment of the invention.

Generally in Reaction Step (1) the 2-(chloro, bromo or nitro)-4-(chlorosulfonyl)benzoyl chloride reaction product of Reaction Step (3) preferably is reacted with an equimolar amount of a reducing agent, preferably sodium or potassium sulfite, along with a base, preferably an inorganic base, having a sodium, potassium or ammonium cation. Such base are sodium or potassium hydroxide, sodium or potassium bicarbonate or ammonium hydroxide. Preferably the base is sodium bicarbonate. Generally about 3 or more mmol of the are used, preferably between about 4.0 to 4.5 moles. The reaction preferably should be run at a pH of about 7-9. The reaction is run in water, optionally in the presence of a non-miscible organic solvent. During Reaction Step (1), the sulfonyl chloride group is reduced to the sodium, potassium or ammonium salt of the corresponding sulfinate and the acid chloride group is hydrolyzed to the sodium, potassium or ammonium salt of the benzoic acid. Reaction Step (1) is preferably run at a temperature above about 0° C., more preferably between about 20° C. to about 100° C., even more preferably between about 30° C. to about 75° C. and most preferably between about 40° C. and about 50° C. when "R" is nitro, the reaction preferably should be run at a temperature between about 10° C. to about 20° C. The reaction at the most preferably temperature or above is very quick and normally takes less than 15 minutes.

The reaction product is soluble in the aqueous solvent and normally is not isolated.

Reaction Step (2) is carried out by adding a mole of the sodium, potassium or ammonia salt of an halocarboxylic acid of the structural formula

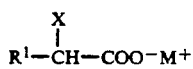

wherein $R^1$ is hydrogen, $C_1$-$C_3$ alkyl, preferably methyl, ethyl or n-propyl, more preferably hydrogen; M is sodium, potassium or ammonium; and X is chloro, bromo or iodo, preferably chloro, to the aqueous reaction product of Reaction Step (1). In the alternative, the above salt of an α-halocarboxylic acid can be formed in situ by adding equal molar amounts of an α-halocarboxylic acid of the structural formula

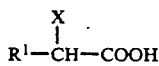

where $R^1$ and X are as defined with an inorganic base having a sodium, potassium or ammonium cation. Such bases are the same as defined in Reaction Step (1). The reaction is carried to completion by heating the reaction mixture to reflux for about 6–48 hours. The reaction time can be reduced by heating the reaction mixture at higher temperatures under pressure.

Generally in Reaction Step (3), the reaction between the benzoic acid reactant and the thionyl chloride is run in conventional equipment using excess thionyl chloride and at least 5 mole percent of the dimethylfonamide (DMF) catalyst. Preferably, the reaction is run in an inert solvent such as toluene or ethylene dichloride, or excess thionyl chloride can serve as the solvent. Preferably, the reaction is run at a temperature between about 50° C. to about 100° C. in the absent of moisture. The reaction product is recovered by conventional techniques such as separating solids by filtration and evaporating excess solvent from the filtrate to yield the desired reaction product.

As previously recited, an embodiment of this invention is directed to a process for preparing 2,4-disubstituted benzoic acid compounds having the structural formula

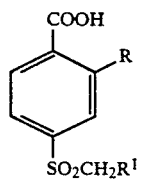

wherein R is chloro, bromo or nitro and $R^1$ is hydrogen or $C_1$-$C_3$ alkyl, by (1) reacting a compound having the structural formula

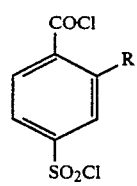

wherein R is as defined with a reducing agent along with a base, preferably an inorganic base, having a sodium, potassium or ammonium cation in an aqueous medium to prepare an intermediate having the structural formula

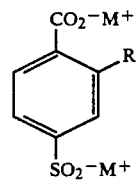

wherein R is chloro, bromo or nitro and M is hydrogen, sodium, potassium or ammonium, followed by (2) reacting the intermediate from step (1) with a salt having the structural formula

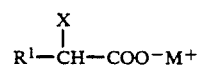

wherein X is chloro, bromo or iodo; $R^1$ is hydrogen or $C_1$-$C_3$ alkyl and M is sodium, potassium or ammonium to prepare a salt of a benzoic acid having the structural formula

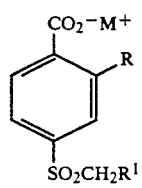

wherein M, R and $R^1$ are as defined and finally acidifying the salt to prepare the desired product having the structural formula

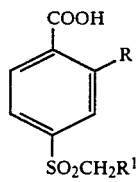

wherein R and $R^1$ are as defined.

The intermediate benzoic acids of Reaction Step (2) can easily be converted to their respective acid chlorides and then to their acid cyanides, if desired, by the following two reactions. First, a mole of oxalyl chloride and a catalytic amount of dimethylfonamide in a suitable solvent such as methylene chloride is heated at a temperature of 20° to 40° C. for 1 to 4 hours with a mole of the intermediate benzoic acid. The corresponding benzoic acid cyanide can easily be prepared from the benzoic acid chloride by reaction with cuprous cyanide at a temperature of 50° to 220° C. for 1 to 2 hours.

The following series of examples teach the synthesis of representative intermediate compounds of this invention and the processes of this invention. The structures of all compounds of the examples and tables were verified by nuclear magnetic resonance (NMR), infrared spectroscopy (IR) and mass spectroscopy (MS).

EXAMPLE 1

2-CHLORO-4-CHLOROSULFONYL)BENZOYL CHLORIDE

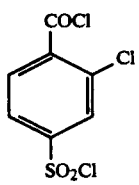

A 25 milliliter (mL) round bottom flask equipped with reflux condenser, thermometer, and magnetic stirrer was charged with 3.2 grams (g) [10.0 millimole (mmol)]of the potassium salt of 2-chloro-4-sulfobenzoic acid (85 wt. % pure), 10 mL (140 nmol) of thionyl chloride and 0.03 g (0.5 mmol) of dimethylfordamide (DMF). After heating for one hour at 60° C., the cooled reaction mixture was diluted with 10 mL of toluene, filtered and evaporated to afford 2.55 g (100% yield) of 2-chloro-4-(chlorosulfonyl)benzoyl chloride as a brown oil.

EXAMPLE 2

2-CHLORO-4-(METHYLSULFONYL)BENZOIC ACID USING CHLOROACETIC ACID AND SODIUM HYDROXIDE

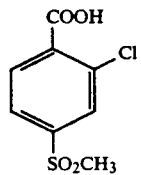

A 250 mL round bottom flask equipped with a reflux condenser, thermometer, and magnetic stirrer was charged with 9.2 g (73 mmol) of sodium sulfite, 24.6 g (292 mmol) of sodium bicarbonate and 80 mL of water. The resulting slurry was heated to 50° C., and 20.0 g (70 mmol) of 2-chloro-4-(chlorosulfonyl)benzoic acid was added over 15 . After heating at 50° C. for three hours, chloroacetic acid (10.4g., 110 mmol) and 5.7 mL (110 mmol) of 50% aqueous sodium hydroxide were added sequentially to the aqueous solution of 2chloro-4-sulfinylbenzoic acid, and the reaction mixture heated to reflux. After heating for 19 hours, the reaction mixture was allowed to cool to ambient temperature and acidified with dilute HCl. The precipitated solids were collected by filtration, washed with dilute HCl and dried to give 17.4 g of 2-chloro-4-(methylsulfonyl)-benzoic acid as a white solid. The solid was assayed at 85% purity, corresponding to an overall yield of 89%.

EXAMPLE 3

2-CHLORO-4-METHYLSULFONYL)BENZOIC ACID

USING THE SODIUM SALT OF CHLOROACETIC ACID

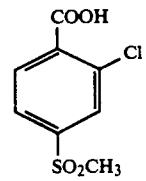

A 100 mL round bottom flask equipped with a reflux condenser, thermometer, and magnetic stirrer was charged with 4.6 g (37 mmol) of sodium sulfite, 12.3 9 (146 mmol) of sodium bicarbonate and 40 mL of water. The resulting slurry was heated to 75° C. and 10 g (33 mmol of chloro-4-(chlorosulfonyl)benzoyl chloride was added slowly. After stirring at 75° C. for 2 hours, 6.4 g (55 mmol) of the sodium salt of chloroacetic acid was added and the reaction mixture heated at reflux for 21 hours. The cooled reaction mixture was acidified with dilute HCl and extracted with ethyl acetate. The organic layer was dried with magnesium sulfate and evaporated to dryness to afford 7.5 g of 2-chloro-4-(ethylsulfonyl)benzoic acid as a white solid. This material was shown to be 87% pure, representing an 85% overall yield.

EXAMPLE 4

2-BROMO-4-(CHLOROSULFONYL)BENZOYL CHLORIDE

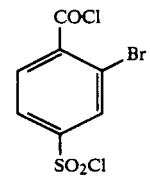

A 100 mL round bottom flask equipped with reflux condenser, temperature controller and magnetic stirrer was charged with 8.8 g (28 mmol) of the potassium salt of 2-bromo-4-sulfobenzoic acid, 21.5 mL (301 mmol) of thionyl chloride, and 0.12 g (1.7 mmol) of DMF. After heating for five hours, the cooled reaction mixture was filtered and evaporated to afford the desired product, 2-bromo-4-(chlorosulfonyl)benzoyl chloride.

EXAMPLE 5

2-BROMO-4-(METHYLSULFONYL)BENZOIC ACID

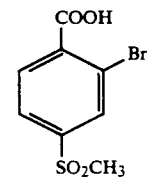

A 50 mL round bottom flask equipped with a reflux condenser, thermometer and magnetic stirrer was charged with 1.6 g (13 mmol) of sodium sulfite, 4.2 g (50 mmol) of sodium bicarbonate and 20 mL of water. The resulting slurry was heated to 75° C. and 4.0 g (13 mmol) of 2-bromo-4-(chlorosulfonyl)benzoyl chloride was added over 30 minutes. After heating at 75° C. for one hour, chloroacetic acid (1.8 g, 19 mmol) and 1.0 mL (19 mmol) of 50% aqueous sodium hydroxide were added sequentially to the aqueous solution of 2-bromo-4-sulfinylbenzoic acid, and the reaction mixture heated to reflux. Additional chloroacetic acid (2.0 g) was added as necessary to drive the reaction to completion. After heating for 16 hours, the reaction mixture was allowed to cool to ambient temperature and acidified with concentrated HCl. The precipitated solids were collected by filtration and dried to give 1.6 g of 2-bromo-4-(methylsulfonyl)benzoic acid, corresponding to a 46% yield.

EXAMPLE 6

2-NITRO-4-(CHLOROSULFONYL)BENZOYL CHLORIDE

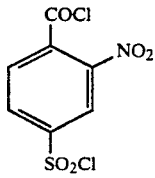

A 250 mL round bottom flask equipped with reflux condenser, thermometer, and magnetic stirrer was charged with 9.0 g (32 mmol) of the salt of 2-nitro-4-sulfobenzoic acid, 10.7 L (142 mmol) of thionyl chloride, 0.23 g (3.2 mmol) of DMF and 40 mL of toluene. After heating for one hour at 85° C., the cooled reaction mixture was filtered and evaporated to afford 8.2 g (92% yield) of 2nitro-4-(chlorosulfonyl)-benzoyl chloride as an amber oil.

EXAMPLE 7

2-NITRO-4-(METHYLSULFONYL)BENZOIC ACID

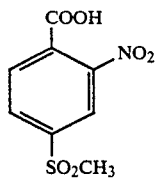

A 100 mL round bottom flask equipped with a reflux condenser, thermometer and magnetic stirrer was charged with 1.9 g (15 mmol) of sodium sulfite, 5.1 g (60 mmol) of sodium bicarbona+ and 20 mL of water. The resulting slurry was cooled to 15° C. and 4.0 g (14 mmol) of 2-nitro-4(chlorosulfonyl)benzoyl chloride was added over 5 minutes. The reaction mixture was stirred at 15° C. for three hours and then at ambient temperature overnight. After warming to 40° C., 3.1 g (27 mmol) of the sodium salt of chloroacetic acid was added to the aqueous solution of 2 nitro-4-sulfinylbenzoic acid and the reaction mixture heated to reflux. After heating for 7 hours, the reaction mixture was allowed to cool to ambient temperature, diluted with 30 mL of water and washed with 50 mL of ethyl acetate. The aqueous layer was acidified with concentrated HCl and extracted with 75 mL of ethyl acetate. The organic solution was concentrated to afford 3.0 g (87% yield) of 2-nitro-4-(methylsulfonyl)benzoic acid as a pale yellow solid.

What is claimed is:

1. A process for preparing 2-(chloro, bromo or nitro)-4-(alkysulfonyl) benzoic acid compounds having the structural formula

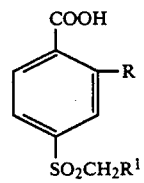

wherein R is chloro, bromo or nitro and $R^1$ is hydrogen or $C_1$-$C_3$ alkyl, comprising (1) reacting a compound having the structural formula

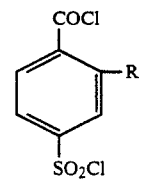

wherein R is as defined with a reducing agent along with a base having a sodium, potassium or ammonium cation ($M^{3\oplus}$) in an aqueous medium to prepare a compound having the structural formula

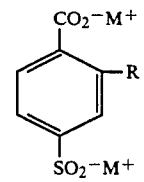

wherein R is chloro, bromo or nitro and M is sodium, potassium or ammonium and (2) reacting the prepared compound from step (1) with an α-halocarboxylic acid compound having the structural formula

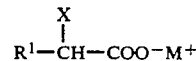

wherein X is a chloro, bromo or iodo; $R^1$ is hydrogen or $C_1$-$C_3$ alkyl; and M is sodium, potassium or ammonium, to prepare a benzoic acid compound having the structural formula

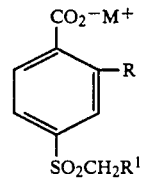

wherein M, R and $R^1$ are as defined, and finally acidifying the compound to prepare the desired product having the structural formula

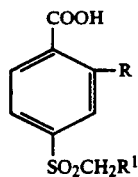

wherein R and $R^1$ are as defined.

2. The process of claim 1 wherein R is chloro, $R^1$ is hydrogen, M is sodium and X is chloro.

3. The process of claim 1 wherein R is nitro, $R^1$ is hydrogen, M is sodium and X is chloro.

4. The process of claim 1 wherein the α-halocarboxylic acid compound of step (2) is prepared in situ from about equal molar amounts of an α-halocarboxylic acid of the structural formula

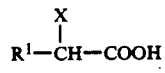

wherein $R^1$ and X are as defined and a base having sodium, potassium or ammonium as the cation.

5. The process of claim 1 wherein the base is an inorganic base having a sodium, potassium or ammonium cation.

* * * * *

UNITED STATES PATENT AND TRADEMARK OFFICE
CERTIFICATE OF CORRECTION

PATENT NO. : 5,008,448
DATED : April 16, 1991
INVENTOR(S) : Richard W. Brown

It is certified that error appears in the above-indentified patent and that said Letters Patent is hereby corrected as shown below:

Title page, item [54], and col. 1, line 4, should read --alkyl-sulfonyl--
Column 8, line 31, "($M^{30}$) should read --($M^+$)--.

Signed and Sealed this

Third Day of January, 1995

BRUCE LEHMAN

*Attest:*

*Attesting Officer*      *Commissioner of Patents and Trademarks*